United States Patent [19]

Buckley et al.

[11] Patent Number: 4,557,386
[45] Date of Patent: Dec. 10, 1985

[54] SYSTEM TO MEASURE GEOMETRIC AND ELECTROMAGNETIC CHARACTERISTICS OF OBJECTS

[75] Inventors: Bruce S. Buckley, San Jose; Edward M. Buckley, Milpitas; Roy H. Reichwein, San Jose, all of Calif.

[73] Assignee: Cochlea Corporation, San Jose, Calif.

[21] Appl. No.: 508,122

[22] Filed: Jun. 27, 1983

[51] Int. Cl.⁴ .................... B07C 5/344; G01S 9/66
[52] U.S. Cl. .................... 209/556; 209/527; 209/558; 209/571; 209/590; 367/8; 367/11; 367/96; 367/126; 414/730; 901/15; 901/45; 901/46
[58] Field of Search .......... 209/527, 555, 556, 558, 209/567, 570–572, 576, 590; 367/8, 87, 96, 902, 7, 11, 99, 100, 103, 104, 123, 126, 151; 181/123; 73/602, 628; 414/730; 901/15, 45, 46

[56] References Cited

U.S. PATENT DOCUMENTS

| | | | |
|---|---|---|---|
| 3,438,493 | 4/1969 | Goble | 209/590 |
| 3,679,020 | 7/1972 | Sondhi | 367/7 |
| 3,717,843 | 2/1973 | Farrah et al. | 367/8 |
| 3,736,552 | 5/1973 | Sessler et al. | 367/7 |
| 3,803,606 | 4/1974 | Lebail et al. | 367/8 X |
| 3,804,270 | 4/1974 | Michaud et al. | 209/939 X |
| 3,918,297 | 11/1975 | Rocha | 367/87 X |
| 3,975,261 | 8/1976 | Beck | 209/590 X |
| 4,049,123 | 9/1977 | Fegley et al. | 209/555 |
| 4,169,257 | 9/1979 | Smith | 367/123 |

OTHER PUBLICATIONS

IBM Technical Disclosure Bulletin, vol. 18, No. 8, pp. 2665–2667, Affinito et al., Jan. 1976.

Primary Examiner—Randolph A. Reese
Assistant Examiner—Edward M. Wacyra
Attorney, Agent, or Firm—Robert Shaw

[57] ABSTRACT

A system to measure geometric and electromagnetic characteristics of objects. Wave energy of a single frequency (or very narrow band of frequencies) is directed upon an object which reflects (or otherwise interacts with) the wave energy. The reflected wave energy is sensed by many spatially spaced sensors to provide electric signals whose amplitude and phase components are combined to give a quantity from which geometric and/or electromagnetic characteristics of the object can be ascertained.

35 Claims, 14 Drawing Figures

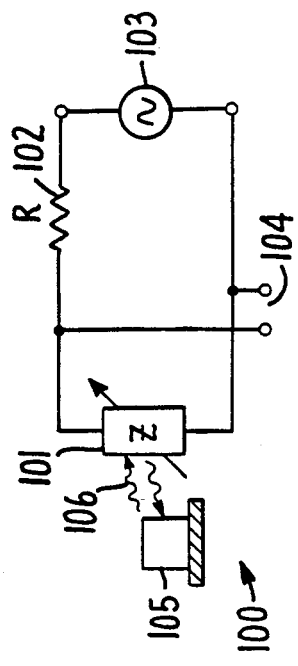
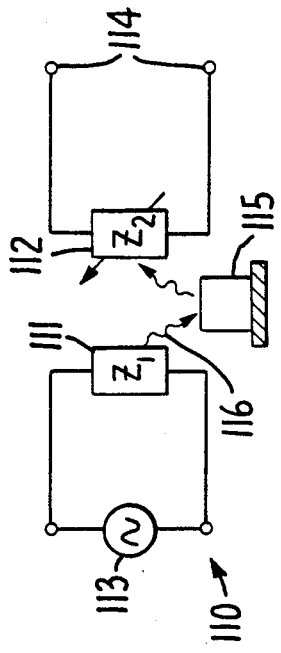
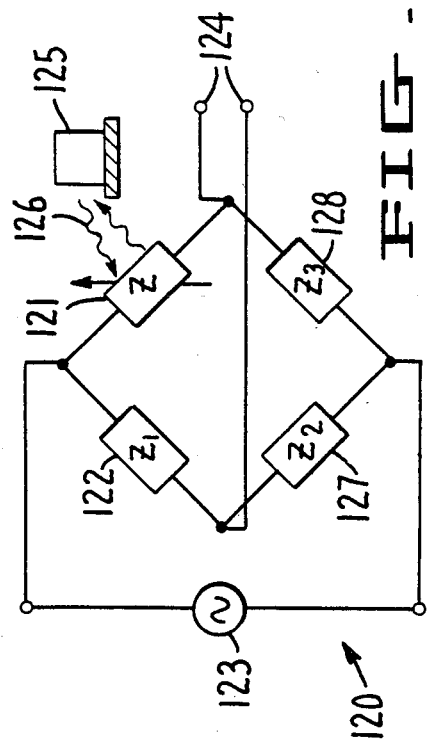
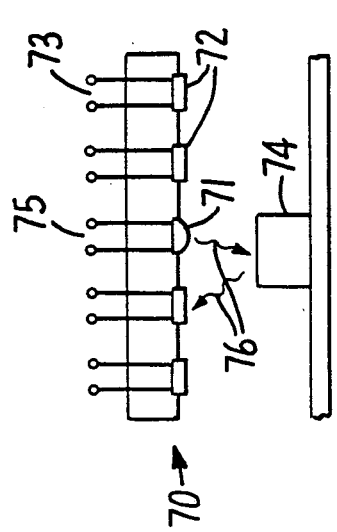
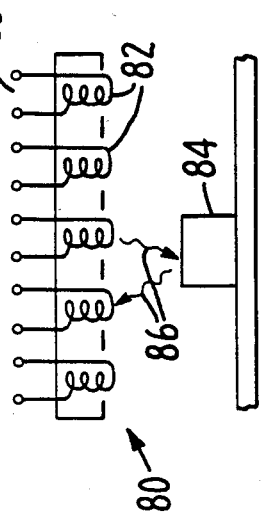
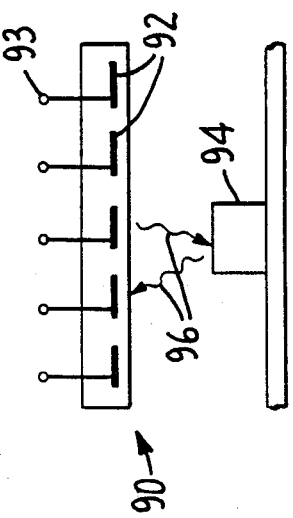

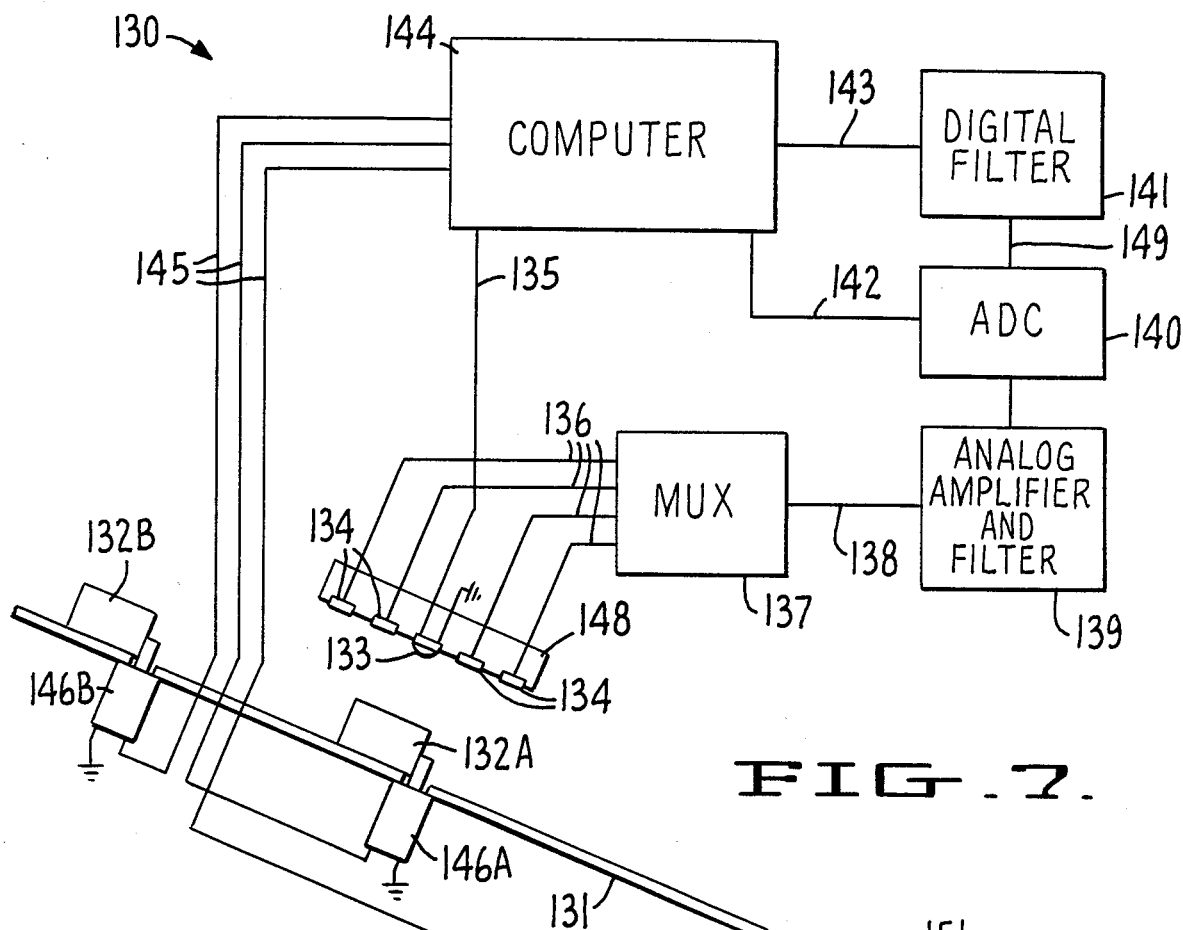
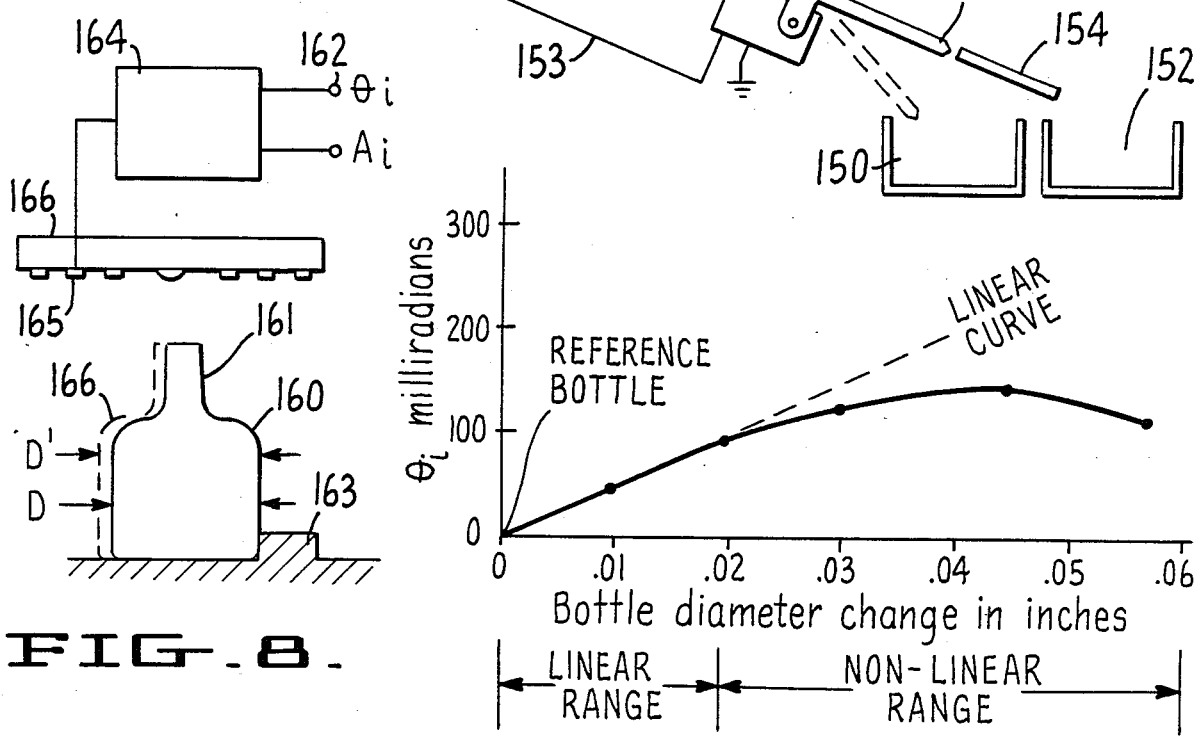
FIG. 8.
FIG. 9.

SYSTEM TO MEASURE GEOMETRIC AND ELECTROMAGNETIC CHARACTERISTICS OF OBJECTS

The present invention relates to systems to measure geometric and electromagnetic characteristics of objects.

Attention is called to U.S. Pat. Nos. of the inventor Shawn Buckley herein: 4,095,475; 4,200,921; and 4,287,769.

There is a continuing need to emulate the human senses in connection with, among other things, industrial robots. A most difficult problem is that of teaching a robot a new job. Systems to make parts in the million-lot amounts presents one kind of problem, but to fabricate parts in hundred-lot quantities is not particularly attractive using presently-available techniques. For these types of parts, the costs of custom tooling is enormous and cannot be spread out over millions of parts. Moreover, even engineering costs can become high in cases when parts handling systems must be specially designed or which require time-consuming alignment or programming of components.

The costs of part change-over and small volume part production can be reduced if manufacturing systems can be made versatile: changed by programs in software rather than mechanical hardware. Industrial robots are very versatile because simple changes in their computer programs allow the robot to change to a different manufactured part in short order. However, the need arises for a robot to sense the position or shape of a new part, quickly and with little manual intervention and thereafter to sense similar parts to determine if their shape or position is correct. The solution to such a need will allow robots and other manufacturing equipment to deal with parts made in small quantities.

OBJECTIVES OF THE INVENTION

Accordingly, it is an objective of this invention to provide a method of detecting the shape, orientation or position of objects using single frequency continuous wave energy which is emitted by a transmitter. The objects interfere with the waves which are subsequently detected by an array of receivers giving continuous wave electrical signals as outputs. The outputs are amplified, filtered and processed to give digital data representing the amplitude and phase of the received signals. This amplitude and phase information is analyzed to determine the characteristics of the objects.

Another objective is to use the characteristics of the objects to guide the manipulation of the objects; such manipulation may be by industrial automation equipment including parts feeders and sorters or by robots or other object positioning systems.

A further objective is to provide a method to analyze the amplitude and phase information using cost functions to determine the characteristics of the object.

A still further objective is to provide a method of analyzing the amplitude and phase information from the receivers which adjust over many trials to be sensitive to particular characteristics of the objects.

These and still further objectives are addressed hereinafter.

The foregoing objectives are achieved, generally, in a method of (and apparatus for) measuring geometric (i.e., shape, orientation, position, etc.) and electromagnetic characteristics of an object, that include directing wave energy of a single frequency upon the object; directing the wave energy which interacts with the object upon an array of spatially separated or spaced wave energy sensors; processing the signals from the wave energy sensors into amplitude and phase information for each said sensor; and combining the amplitude and phase information of the array of sensors to provide a quantity that represents the geometric and/or electromagnetic characteristics of the object.

The invention is hereinafter described with reference to the accompanying drawing in which:

FIG. 1 is a diagrammatic representation of a system to transmit and receive acoustic wave energy in a system fabricated in accordance with the present teachings;

FIGS. 2 and 3 are respectively diagrammatic representations of inductive and capacitive sensor/receiver transducers;

FIG. 4 is a diagrammatic representation of a system wherein a single transducer is employed both to send and to receive wave energy, the term self-impedance being used herein to denote such a transducer;

FIG. 5 is a diagrammatic representation of a system wherein one transducer (or several) sends wave energy and other transducers receive wave energy, the term mutual impedance being used herein to denote such arrangement:

FIG. 6 is a diagrammatic representation of a bridge circuit used to transmit and receive wave energy;

FIG. 7 is a diagrammatic representation of a sorting system employing the present concepts;

FIG. 8 is a diagrammatic represention of a scheme to sense size changes of an object;

FIG. 9 is a graph showing phase of wave energy versus bottle diameter in the system of FIG. 8;

DESCRIPTION OF THE INVENTION

Figure 10:
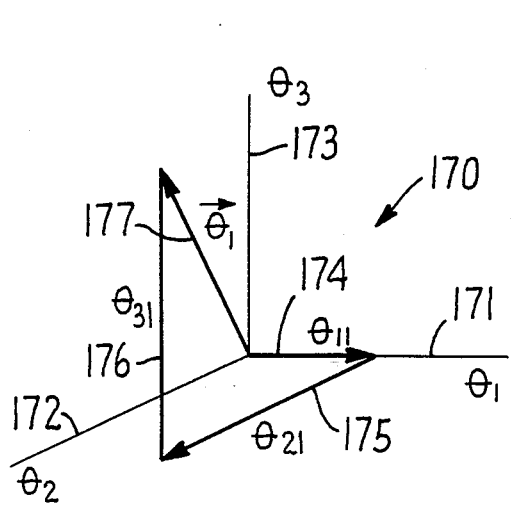
FIGS. 10 and 11 are a phase space cost function wherein distance between space vectors represents cost function.

The present invention is multi-faceted; it applies to a parts inspection system of many like parts; it applies to periodic inspection of the same object such as a cutting tool or the like to detect geometric changes in the object; and it applies to industrial robots where simple verification of the robot's manipulation of objects is required. The term geometric characteristic or geometric parameter as used herein includes actual contour changes (e.g., a broken tool) but it includes as well position changes due, for example, to re-orientation of a part or movement between a part and a sensor.

The invention is described here in greatest detail with reference to acoustic wave energy, but, as noted, electromagnetic wave energy can also be used as may also combinations of acoustic wave energy and electromagnetic wave energy. The description is first of a general nature and then more specific, the latter being with reference to an actual system built and used to show the efficacy of the present concepts.

This invention has two aspects, including a data acquisition aspect, previously described in prior U.S. Pat. No. 4,200,921 of the present inventor Bruce Shawn Buckley and a data processing and reduction aspect which is a new mechanism and method of measuring objects under test. First, the data acquisition aspect will be described, noting that improvements have been made which allow both amplitude and phase measurements to be made.

First, a description of the sensors themselves will illuminate the data acquisition aspect of the invention. Sensors are generally either acoustic or electromagnetic, although other sensors which alter amplitude and phase information of continuous wave energy interacting with an object may also be used. One type of sensor is used to produce the wave energy (the transmitter) and another type is used to detect the wave energy (the receiver). In some cases, as will be discussed, a single sensor both produces and detects the wave energy.

Acoustic sensors are composed of transmitter/receiver transducers such that sound waves are transmitted by the transmitter, interact with the object and are picked up by the receivers. FIG. 1 shows an array 70 composed of a transmitter 71 and receivers 72 used to detect the shape of an object 74. Electrical signals input to the transmitter 71 via contacts 75 are transduced into acoustic wave energy 76 which interacts with the object 74. Variations of wave energy 76 are received by the receivers 72 whose output is available on contacts 73.

Electromagnetic sensors are shown in FIG. 2 (inductive sensors) and FIG. 3 (capacitive sensors). While sensors of this sort are quite common in such devices as proximity sensors, their use as a method of detecting an object's shape as part of a multi-element array of sensors using continuous wave energy and interpreted in the manner herein described is wholly new and innovative.

A brief discussion of these sensors and how they may be used in conjunction with the acoustic transducers just described follows. FIG. 2 shows an array 80 with inductive sensors 82 which are simply coils of wire. Electromagnetic wave energy 86 emanating from the sensors 82 interacts with an object 84. Electrical output signals from the sensors 82 is available on contacts 83. Inductive sensors such as the ones described are useful in determining the shape of an object 84 as well as certain magnetic properties of the object such as hardness and alloy.

FIG. 3 shows capacitive sensors 92 fixed to an array 90. The sensors 92 are simply conducting plates which can emanate electromagnetic waves 96 which interact with an object 94. The interaction can be detected via electrical contacts 93 for interpretation by a computer (later discussed). Capacitive sensors such as those described can detect other properties of an object 94 besides shape: material properties of the object 94 such as dielectric constant of certain plastics and the water content of paper products. In addition the presence of people near industrial equipment can be detected as can the shape of faces in certain identification tasks.

The electrical output signals on contacts 73 of the acoustic sensors 72 of FIG. 1 are sinusoidal signals whose amplitude and phase vary according to the shape of the object 74. These signals are subject to the details of the transduction method employed. In general, transducers 71 and 72 may operate by several well-known principles: electret diaphragm coupled to sensitive amplifiers, piezoceramic crystals coupled to sound-collecting diaphragms, "condenser" transducer which couple coils embedded in a diaphragm to a driver coil close by.

For electrical output of electromagnetic transducers such as the sensors 82 and 92 to produce a similar phase and amplitude signal, several principles can be employed. In the following description of these circuits, the generalized impedance Z will be used to represent either an inductor or a capacitor. FIG. 4 shows a self-impedance circuit 100 wherein an impedance 101 is varied by its interaction through electromagnetic wave energy 106 with a part 105. The wave energy 106 is produced by a continuous wave electrical voltage or current source 103 driving current through a resistor 102 and impedance 101. The voltage signal across terminals 104 is characterized by its amplitude and phase which is subsequently interpreted by the computer.

Typically the resistor 102 would be chosen such that the operating frequency of the circuit 100 is near the circuit's break frequency to maximize the change in amplitude and phase with changes in the shape of object 105. Other circuits elements can replace the resistor 102. For example, if a capacitor C coupled with a resistor R is substituted for the resistor 102 and the impedance 101 is an inductor L tuned to the resonance of the LRC circuit, the amplitude and phase characteristics measured at terminals 104 become quite sensitive to changes in the shape of object 105.

The circuit 100 is termed "self-impedance" because the sensors 101 both send and receive electromagnetic wave energy; FIG. 5 is a circuit 110 which is termed "mutual impedance" because one sensor element 111 sends electromagnetic wave energy 116 and other sensors 112 receive the wave energy. An electrical voltage or current source 113 of continuous waves causes the impedance or sensor element 111 to emanate wave energy 116 which interacts with object 115 to change the amplitude and phase signals output on terminals 114. For example, if the impedance 111 and 112 are coils, the mutual inductance between the coils will vary depending on the shape of the object 115; the change can be detected through amplitude and phase differences measured at the output terminals 114.

A third technique for detecting shape and other changes of an object is shown in bridge circuit 120 in FIG. 6. A continuous wave voltage or current source 123 drives the bridge composed of impedances 121, 122, 127 and 128. The bridge is balanced in the usual manner with impedances 121 and 122 chosen to be nearly equal as are impedances 127 and 128. Any change in the impedance 121 due to interaction with a part 125 through electromagnetic wave energy 126, causes a change in the amplitude and phase voltage signals on contacts 124.

It will be noted that all sensors, whether acoustic or electromagnetic, produce changes in the amplitude and phase of electrical signals by which they are connected. The sensors produce wave energy which is either acoustic or electromagnetic or they receive wave energy which interacts with an object to convey information about the object. Usually the information is shape information (i.e., actual contour) but it can also include position and orientation information (which are included herein in the term geometric characteristic or geometric parameter) as well as certain other properties of the part. Each array can include several types of sensors, all of which are interpreted in the same manner by the computer. Moreover, the sensors have been shown as simple linear arrays. In general, the sensors are deployed in a manner which best suits the class of object which they are sensing. For example, inductive sensors for cylindrical objects have inductors through which the objects pass; acoustic sensors deployed in "phased arrays" become sensitive to specific regions of an object.

Now follows a brief discussion of the technique by which the computer interprets the amplitude and phase information from the various sensors. More detail on the method can be found in the U.S. Pat. Nos. 4,095,475 and 4,200,291. The particular application shown is one for sorting parts according to their orientation or shape which uses acoustic sensors for identifying the shape of the object.

An object such as part 132A or 132B in FIG. 7 is transported down a transport mechanism such as chute 131 from its ready position occupied by part 132B. The parts 132A and 132B are fed to the top of the chute 131 (not shown for clarity). Solenoid gate mechanism 146A and 146B, on signals from 145 from a computer 144 ensure that only one part 132A is in the sensing region beneath a sensor array 148. In this example, the sensing array 148 has a transmitting sensor 133 driven by a sinusoidal continuous wave signal from the computer 144.

The wave energy from the transmitting sensor 133 interacts with the part 132A and changes the phase and amplitude of the continuous wave signals detected by receiving sensors 134. These signals are fed to a multiplexor 137 via connections 136; one of the signals is chosen by the computer 144 to be analyzed. The connection 147 is a bus by which the computer 144 signals the multiplexor 137 (MUX) which one of the signals on connections 136 is chosen. The chosen sinusoidal signal from the sensors 134 is fed via connection 138 to an analog amplifier and filter 139 which amplifies or attenuates the signal (as required) and reduces noise at frequencies other than the sinusoidal operating frequency of the transmitted wave energy.

Next, the signal is converted to a digital value in the analog to digital converter (ADC) 140. The filtered sinusoidal signal is sampled at various time intervals as determined by a clock signal fed to the ADC 140 by the computer 144 via connection 142. The sampled values are sent to the digital filter 141 via bus 149 where they are further filtered to remove noise at frequencies other than the transmitted wave energy frequency. Lastly, the filtered data is transmitted to the computer 144 via bus 143 for analysis. Analysis of the filtered data first requires that the data be converted to amplitude and phase information of the received wave energy for the chosen sensor 134. A Fourier transform algorithm, available in the literature, readily converts the digital values to amplitude and phase information.

The computer 144, then, orchestrates data gathering from the sensors 134. First it transmits the operating frequency to the transmitter 133, then directs one after another of the received sensor signals output from the MUX 137 to the filter 139. The computer 144 also determines the timing and the duration of the data sampling in the ADC 140 and, further, receives and analyzes the amplitude and phase information from the digital filter 141. Each sensor signal in turn is so processed; the computer 144 also stores the amplitude and phase information from previously processed sensor signals until all the sensors 134 in the array 148 have been processed.

Once the object 132A has been identified by the analysis techniques to be discussed, it is sorted according to its shape or orientation. The sorting command is sent by the computer 144 via connection 153 to a diverting gate 151. If actuated, the gate 151 allows the object 132A to fall into a bin 150; if the gate is not actuated, the object 132A falls into a bin 152 from a chute 154.

The method by which phase signals are interpreted in prior patents by the inventor Bruce Shawn Buckley was appropriate for shape changes of the object (U.S. Pat. No. 4,095,475) and position changes (U.S. Pat. No. 4,200,921). In order to compare these prior patents with the present invention, only shape and position changes of objects will be discussed henceforth. However, it will be noted that other characteristics of objects are also appropriate to these new methods of interpretation, for example, magnetic characteristics of metal objects such as hardness or dielectric characteristics of objects such as the measurements of human presence.

In the prior patents, a "matrix" approach was used to detect shape and position changes of object. The basis of the matrix approach is linearity: each change in an object—be it shape or position—is linearly proportional to a change in the amplitude and phase information.

As an illustrative example, consider an object, say a bottle 160 in FIG. 8 whose diameter D changes. The bottle 160 is positioned against a stop 163 in the sensing region 161 of an inspection chamber. Amplitude and phase information is recorded for the bottle as just discussed by a system 164. As a simplification, consider simply the phase 162 of a particular sensor 165; let this phase be zero when the measurements are taken of the bottle 160. Another bottle 166 placed against the stop 163 having a slightly larger diameter D' will record a phase 162 different from the zero phase recorded against the "reference" bottle 160. FIG. 9 shows a typical curve of bottle diameter change versus phase in milliradians. The linear range of the sensor 165 is generally quite small—suitable for small changes in the bottle's diameter. When changes of interest (in this case, bottle diameter) are small, then the matrix techniques reported in the previous patents are appropriate.

However, when the changes are large, linearity does not hold and the matrix techniques cannot be employed. Now described are conditions under which the shape changes which occur fall in the non-linear range. Moreover, in the non-linear case objects need not be compared to a reference object as in the linear analysis methods.

For simplicity, again consider only the phase information obtained from the sensors rather than both amplitude and phase information. If an object such as the bottle 160, FIG. 8, is placed against the stop 163 in the sensing region 161 beneath array 166, each of the sensors, such as the sensor 165 will give a phase value $\theta_i$ when processed by the system 164 as discussed earlier. When each phase value 162 is processed for each of N sensors in an array 166, a phase vector results:

$$\vec{\theta} = [\theta_1, \theta_2 \ldots \theta_i \ldots \theta_N]$$

Each object such as the bottle 160 placed against the stop 163 will have a different phase vector which identifies it. The method called "vector matching" identifies one object from another by determining if the phase vector of an object matches the phase vector of a previously measured object. Vector matching is inherently a three-dimensional technique because the wave energy which interacts with the object to produce the phase vector is three dimensional.

The phase vector describes the bottle 160 much as a key fits a cylinder lock. If all the lock pins are moved the proper distance by the key, the key opens the lock.

Similarly, if all the phases in the phase vector are the same as for the bottle 160, the bottle is identified. Just as locks with many lock pins are better at discriminating one key from another, so are phase vectors with many elements better at discriminating one object from another. Of course, the sensors such as the sensor 165 in the array 166 must be separated spatially enough to detect different phases in the first place.

Given a vector for each of several objects, the present invention uses cost functions to determine which object is which. Cost functions combine the vectors in a unique way to give a single scalar number (or cost function) for the multi-element vector. Cost functions may be compared for the different objects. Generally, if a cost function is numerically close to another cost function, the vectors from which they were derived are similar and thus the objects from which the vectors came are similar as well. An unknown object is identified by comparing its cost function to the cost function of a known object. The unknown object is usually most similar to the object whose cost function is closest numerically.

It will be useful to consider a simple case of identifying an unknown object by comparison to only a single known object. The phase vector for the unknown object is:

$$\vec{\theta} = [\theta_1, \theta_2 \ldots \theta_N],$$

where $\theta_i$ is the phase for each of the sensors $1 \ldots N$. For the known object the phase vector is:

$$\vec{\theta} = [\theta_1', \theta_2' \ldots \theta_N']$$

A cost function may be formed from these vectors by subtracting the phases one by one to give a phase difference vector:

$$\vec{\Delta\theta} = [\theta_1 - \theta_1', \theta_2 - \theta_2' \ldots \theta_N - \theta_N']$$

The phase difference vector is combined to give the cost function J by first taking the absolute value of each phase difference and then summing:

$$J = \sum_{i=1}^{N} |\theta_i - \theta_i'| \tag{1}$$

Now the unknown object, even if it were identical to the known object, would have a non-zero cost function. Inaccuracies in measurement of the sensor phases, inaccuracies in positioning the object are among the errors which can make the cost function greater than zero. The absolute value function insures that no negative error cancels a positive error. In practice, the objects themselves vary in shape as well. Shape errors add to the cost function errors due to measurement errors, position and other inaccuracies.

Interpreting the cost functions becomes one of pattern recognition: distinguishing correct objects which have position and acceptable shape errors from incorrect objects which have position and unacceptable shape errors. The simplest method of interpretation is to set a threshold on the cost function. Values above the threshold cannot be classifed as a known object. For example, for determining if an unknown object is among a group of known objects, equation (1) becomes:

$$J_{min} = \min_{j=1}^{M} \left[ \sum_{i=1}^{N} |\theta_i - \theta_{ij}'| \right], \tag{2}$$

where
N is the number of sensors
M is the number of known objects to which the unknown object is compared
$\theta_i$ is the phase of the $i^{th}$ sensor
$\theta_{ij}'$ is the phase of the $i^{th}$ sensor measured for the $j^{th}$ object.

The minimum function $$\left( \min_{j=1}^{M} \right)$$

identifies the object as that associated with the smallest cost function found among the known objects. In addition:

$$J_{min} \leq J_O \tag{3}$$

where $J_O$ is a threshold. If the value of $J_{min}$ is below the threshold $J_O$ then the unknown object is identified as the object with the minimum cost function, if the value $J_{min}$ is above the threshold then the unknown object cannot be identified. Such a threshold is particularly important in sinusoidal wave energy fields as occurs with acoustic sensors 71 and 72 since cost functions do not necessarily increase monotonically as the shape of position of an unknown object diverges from a known object.

Other cost functions are appropriate for other applications. For example, a quadratic cost function uses the same input variables as the absolute value cost function, but combines them differently. A quadratic cost function is:

$$J_{min} = \min_{j=1}^{M} \left[ \sqrt{\sum_{i=1}^{N} (\theta_i - \theta_{ij}')^2} \right] \tag{4}$$

Here the phase differences between the unknown phases $\theta_i$ and the unknown phases $\theta_{ij}'$ (for each of the i sensors and j known objects) are squared and then summed. Quadratic cost functions, by squaring the phase deviations, can over-emphasize measurement errors; they are appropriate when measurement errors are small compared to other errors such as shape and position errors.

The cost functions can be interpreted by referring to an N-dimensional "phase space". In phase space, each sensor adds a dimension: N sensors give an N dimensional phase space. FIG. 10 shows a 3-dimensional phase space 170 having the three coordinate dimensions as the three cartesian axes 171, 172, 173. A phase vector 177 represents an object whose phase vector $\vec{\theta}_1$ has coordinates 174, 175, 176 of $\theta_{11}$, $\theta_{21}$, and $\theta_{31}$.

Figure 11:
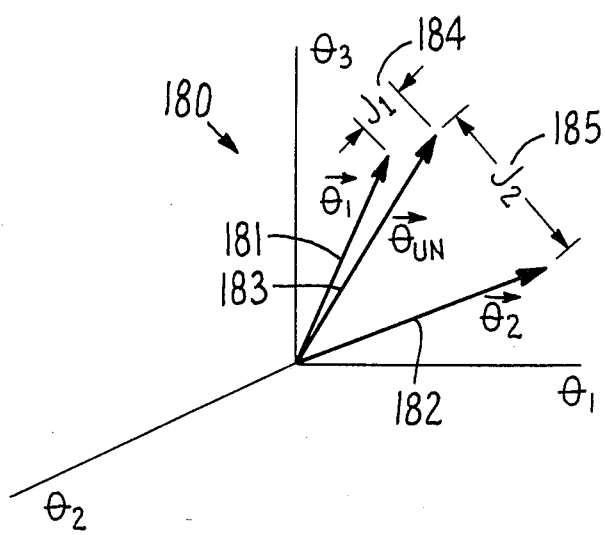

In phase space the distance between phase vectors represents the quadratic cost function. FIG. 11 shows phase space 180 with three phase vectors 181, 182, and 183 respectively as vectors $\vec{\theta}_1$, $\vec{\theta}_2$, and $\vec{\theta}_{un}$. The vectors 181 and 182 represent known objects A and B; the vector 183 represents an unknown object C. The distances 184 and 185 between known object vectors 181 and 182 and the unknown object vector 183 are the cost functions $J_1$ and $J_2$, respectively. In the example shown, $J_1$ has the shortest length 184, so the unknown object is identified as object A since the minimum cost function is that associated with vector 181.

Cost functions such as the ones described in equations (2) and (4) treat each sensor's phase contribution to the cost function equally. A more useful cost function is one in which the contribution from each sensor is weighted by a weighting factor, $W_{ij}$. Weighted cost functions are:

$$J_{min} = \min_{j=1}^{M} \left[ \sum_{i=1}^{N} |\theta_i - \theta_{ij}'| \, W_{ij} \right] \quad (5)$$

for the absolute value cost function, and:

$$J_{min} = \min_{j=1}^{M} \left[ \sqrt{\sum_{i=1}^{N} (\theta_i - \theta_{ij}')^2 \, W_{ij}} \right] \quad (6)$$

for the quadratic cost function.

The weights $W_{ij}$ are usually chosen by measuring several of the j known objects to determine the sensitivity of each sensor's phase to "normal" variations in the objects. Normal variations can be due to an object whose position or shape varies in an acceptable manner. For example, a threaded part is acceptable regardless of where the threads begin with relation to other features of the part. A sensor whose phase was sensitive to such a normal variation would be weighted less than sensor phases without such a sensitivity.

In practice, a weighting which varies as the reciprocal of the standard deviation of phase measurements of known objects has been found to give accurate identification of objects. A useful standard deviation weighting for an absolute value cost function is:

$$W_i = 1/\sigma_{ij}, \quad (7)$$

$\sigma_{ij}$ is the standard deviation of the $i^{th}$ sensor measurements for the $j^{th}$ object. Thus if a sensor has a lot of scatter (i.e., high standard deviations of measurements) either due to measurement variations, shape variations or positional variations, its contribution to the cost function will be reduced compared to other sensors with less measurement scatter. Similarly, reciprocal variance weighting is useful in applications with high measurement variations or in weighting quadratic cost functions.

$$W_{ij} = \frac{1}{\sigma_{ij}^2} \quad (8)$$

A second technique for determining if an object is the correct one, whether or not linearity exists between dimension change and phase change, is called adaptive analysis. Such techniques use a weighting of the sensor phase changes much as the cost function techniques previously discussed. However, the "weights" are determined by a learning or adaptive method rather than simply by measuring statistical scatter parameters.

Figure 12:
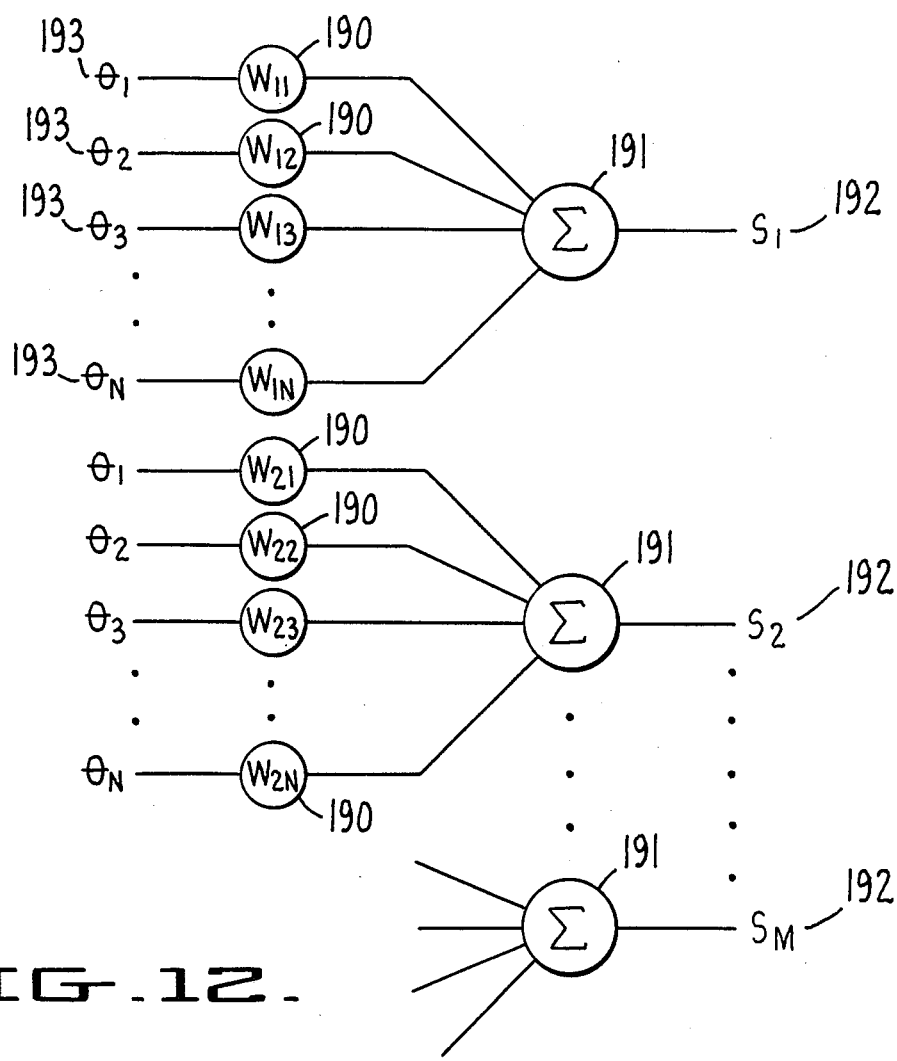
FIG. 12 shows a scheme for weighting inputs to identify an unknown object.

To be sure, learning methods are common in the design of optimum filters such as discussed in "Adaptive Filters" by B. Widrow in Objects of Network and System Theory (Holt, Rinehart & Winston, 1970). The application of these techniques to measuring wave characteristics of continuously transmitted energy waves for the determination of an object's characteristics is unique. FIG. 7 shows an object 132 which is measured acoustically by determining amplitude and phase wave characteristics (henceforth simply phase measurements for clarity) and comparing them to previously determined characteristics to give difference signals $(\theta_i - \theta_{ij}')$ measured. FIG. 12 shows a method by which several objects 132 (FIG. 7) can be distinguished after repeated measurements of several of the objects 132 which differ in a non-linear manner with respect to the phase signals $(\theta_i)$ measured. In FIG. 12, the signals 183 represent $\theta_i$ multiplied by weights 190 such as $W_{11} \ldots W_{1N}$; the resulting values are summed together in summers 191 to give an output value 192 for each of several possible objects 132. Here each output value $S_1 \ldots S_M$ represents a different object 132 being learned. Mathematically the output values 192 have a similar form to the cost functions just discussed:

$$S_j = \sum_{i=1}^{N} W_{ij} \theta_i, \quad (9)$$

where
$W_{ij}$ are the weights 190
$\theta_i$ are the input signals 193
$S_j$ are the output values 192.

The difference is in how the weights are determined. In an adaptive analysis of the objects, the weights are initially set to random values and a "learning" or calibration procedure is performed. Various objects 132 are positioned under the transducer array 148 and phase signals $\theta_1 \ldots \theta_N$ are found.

As each object 132 is measured, one of the output values 192 will have a higher value than the others. The first object 132A, for example, might have its signals 192 such that, when multiplied by the weights $W_{21} \ldots W_{2N}$ the output value $S_2$ is the highest of the outputs 192. The output $S_2$ then becomes associated with the object 132A. Another object 132B might become associated with $S_4$ and so forth, each distinct object 132 being associated with an output 192.

Next, other objects which are similar to objects 132A and 132B are placed under the array 148 and measured. These other objects might be different in shape, in position or in orientation from the first object measured. Hence their output values 192 might or might not assign the proper object. If the correct assignment is made, the values of the weights 190 associated with the correct output signal 192 are increased in value while the weights 190 associated with other output signals 192 are reduced in value. Hence, for an object 132 compared to its initial output signal, the tendency is to reinforce further correct assignments: with larger weights 190 the particular output value 192 would have an even larger value after a proper assignment.

On the other hand, if the assignment was incorrect a different strategy applies. In this case the weights 190 associated with the incorrect output value 192 are reduced while the weights 190 associated with the other output values 192 are increased. Reduced weights 190 of the offending output 192 tend to prevent it from having a large output value in the future. Thus, correct outputs are "rewarded" but incorrect ones are "punished".

Figure 13:
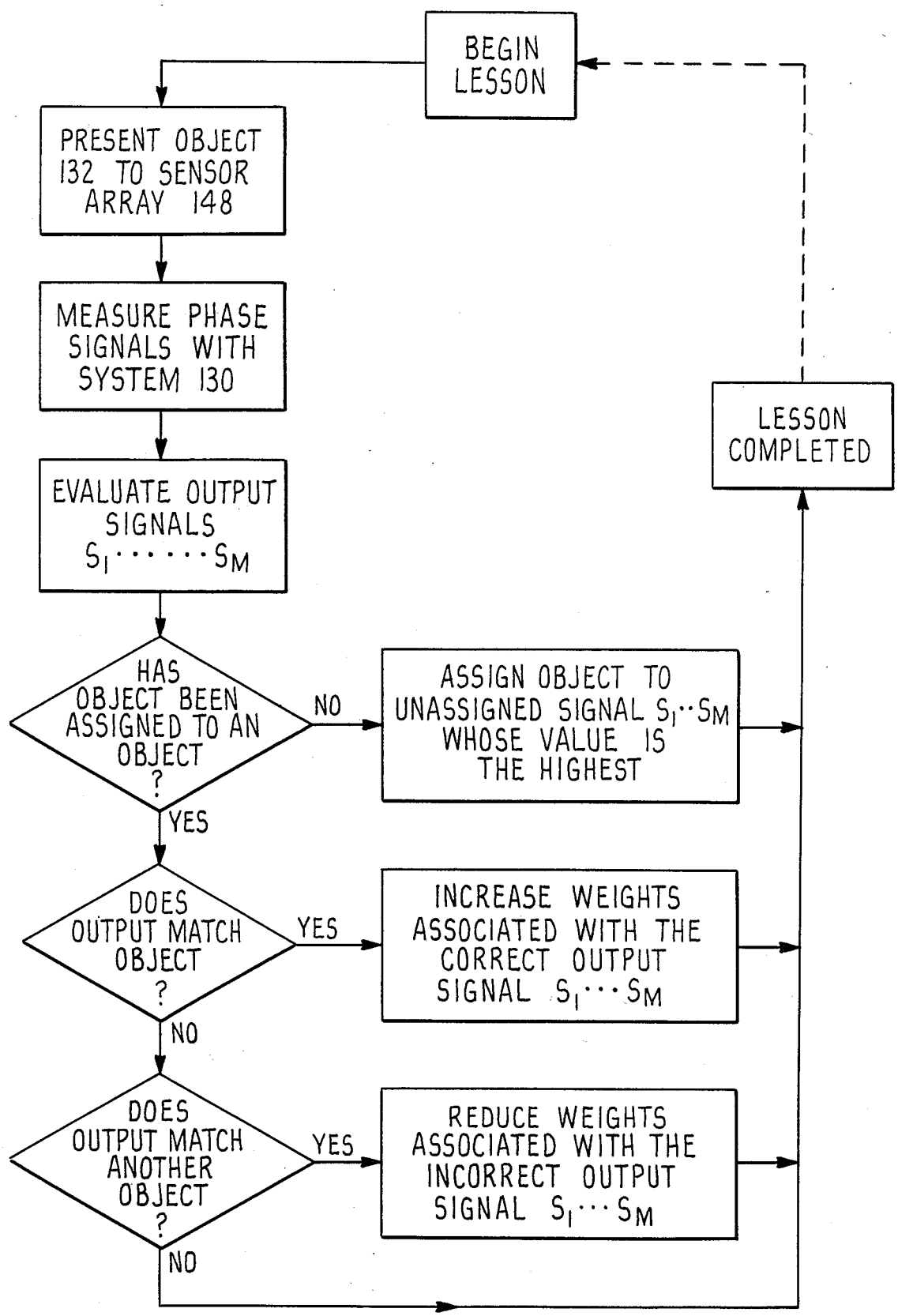
FIG. 13 is a flow chart for the adaptive approach to identification of objects exemplified by FIG. 12.

FIG. 13 gives a flow diagram for the adaptive method just discussed. It will be noted that the method presented is a general one and can have different, but related, calculations involved. For example, the inputs 193 can be binary signals such as discussed in current application Ser. No. 290,784 (now U.S. Pat. No. 4,479,241); the outputs 192 may have weights 190 so structured that they are in binary form or the weights 190 may even include positive and negative values rather than the positive ones just described. The important point is that as correct assignments are found, the weights are altered in a way to enhance future correct assignments while incorrect assignments which tend to reduce future incorrect assignments.

Once the weights are determined for a particular set of objects 132A . . . 132N, then other similar objects can be identified using the weights. The method tends to adjust to the proper set of weights required, in combination, to specify between the various objects. During this "recognize" procedure, unknown objects placed under the transducer array 148 will give a maximum output value 192 to the signal $S_1 \ldots S_M$ which most closely fits the learned objects 132A . . . 132M despite the variations in shape, position or orientation that the unknown object has. As in the cost function method the closeness of the output value 192 to the output value of a perfect object is an indication of closeness of fit. By measuring this difference in output value of the maximum signal $S_1 \ldots S_M$, objects which vary radically from any of the trained or known objects 132A . . . 132M may be rejected.

In general, either the cost function approach or the adaptive approach can be expressed as:

$$X_j = g\left[\sum_{i=1}^{N} W_{ij} f(A_i, \theta_i)\right], \quad (10)$$

where
  $X_j$ is the desired output for a particular object j
  g is a functional relationship
  $W_{ij}$ is a weighting function chosen for each sensor i and each object j
  f is another functional relationship
  $A_i$ is the amplitude of each sensor i
  $\theta_i$ is the phase of each sensor i.

The desired output $X_j$ for each object is used to manipulate the object. In FIG. 7, the manipulation is by sorter gate 151 directed by the computer 144 acting on the amplitude and phase information from sensors 134. In a punch press safety system, the computer would identify humans (or other errant conditions) near the punch dies and stop the press.

Figure 14:
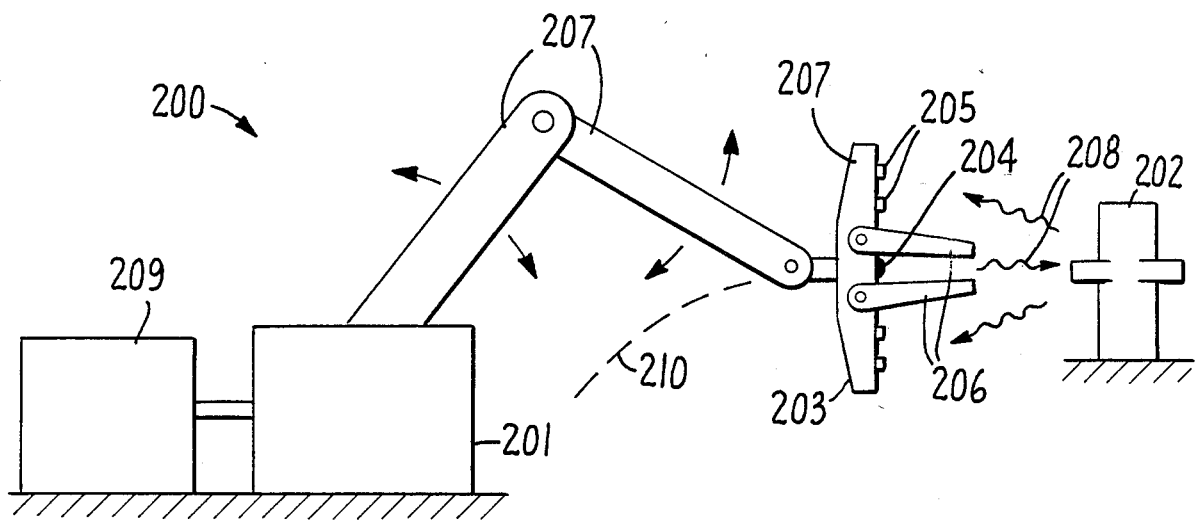
FIG. 14 is a diagrammatic representation of a robot that embodies the present inventive concepts.

In other systems, the desired outputs $X_j$ are suitable for guidance and control. FIG. 14 shows a robot 201 as part of a system 200 used to manipulate an object 202. Movable joints 207 of the robot 201 position a gripper 206 and a sensor array 203 relative to the object 202. Wave energy 208 emitted from transmitter 204 and detected by receivers 205 is converted to amplitude and phase information for each sensor 205 and subsequently analyzed by a computer 209 by the methods just described.

As the gripper 206 approaches the object 202, desired outputs $X_j$ verify that the object's position relative to the gripper is correct for each position j of the gripper's path 210. Thus, if the object 202 has moved or is the wrong object or is otherwise errant compared to a previous calibration, the values of $X_j$ will exceed their threshold (such as $J_O$ in equation 3) and the robot 201 can be stopped before damage occurs.

More than simply detecting faults of the object 202, the outputs $X_j$ may also guide the gripper 206 to proper manipulation of the object 202. For example, if the object 202 has a different position, as the gripper approaches the values of $X_j$ will be higher than when the object is in its initially calibrated position. The values $X_j$ represent the deviation of the object from its correct position. By varying the gripper's trajectory 210 from the nominal other values of $X_j$ will be determined by the computer 209. By seeking those trajectory variations which minimize $X_j$, the gripper 206 will move along the best estimate of the trajectory 210 despite errors in gripper or object position or orientation. Minimizing $X_j$ is performed by computer 209 using hill-climbing "algorithms" which measure the values of $X_j$ along the trajectory 210 and for small deviations away from that trajectory. It will be noted that hill-climbing algorithms are appropriate for minimizing $X_j$ by minimizing (i.e., hill-climbing) the reciprocal of $X_j$.

Further modifications of the invention herein disclosed will occur to persons skilled in the art and all such modifications are deemed to be within the scope of the invention as defined by the appended claims.

What is claimed is;

1. A method of measuring at least one of the geometric and electromagnetic characteristics of an object, that comprises:
  directing continuous wave energy of a single frequency upon the object which interacts with same;
  detecting the continuous wave energy which emanates from said object by virtue of the wave energy directed thereupon by an array of spaced apart wave energy sensors to provide signals;
  processing the signals from the sensors into amplitude and phase information for each of said sensors;
  combining said amplitude and phase information in the signals of the array of sensors to provide a quantity $X_j$ which represents said at least one of the geometric and electromagnetic characteristics of said object, wherein $$X_j = g\left[\sum_{i=1}^{N} W_{ij} f(A_i, \theta_i)\right],$$

where
  $X_j$ is the desired output for a particular object j,
  g is a functional relationship,
  $W_{ij}$ is a weighting function chosen for each sensor i and each object j,
  f is another functional relationship,
  $A_i$ is the amplitude of the signals of each sensor i,
  $\theta_i$ is the phase of the signals of each sensor i; and
  acting upon said object on the basis of said quantity.

2. A method as claimed in claim 1 wherein said acting comprises manipulating said object.

3. A method as claimed in claim 1 wherein said acting comprises guiding and manipulating said object along a predetermined trajectory.

4. A method as in claim 1 wherein said combining of amplitude and phase information includes a weighting factor for each sensor signal.

5. A method as in claim 4 wherein said weighting factor is determined statistically from many previous measurements on objects similar to said objects giving weight to each sensor's amplitude and phase information in accordance with the repeatibility of said measurements.

6. A method as in claim 4 wherein said weighting factor for each sensor signal is adjusted over previous measurements to become sensitive to particular characteristics of the object.

7. A method as in claim 6 wherein adjustment of said weighting factor is based on the correctness of said quantity for said previous measurements.

8. A method as in claim 1 wherein said quantity is compared with previously determined quantities obtained in like manner from similar objects and the object is acted upon on the basis of the comparison.

9. A method as in claim 8 wherein said quantity is used as a basis to manipulate said objects.

10. A method as in claim 8 wherein said quantity is used to guide the manipulation of said object along a predetermined trajectory.

11. A method as in claim 8 wherein said combining of amplitude and phase information includes a weighting factor for each sensor signal.

12. A method as in claim 11 wherein said weighting factor is determined statistically from said similar objects in accordance with the repeatibility of said previously determined quantities.

13. A method as in claim 11 wherein said weighting factor for each sensor signal is adjusted over previous measurements to become sensitive to particular characteristics of said object.

14. A method as in claim 13 wherein adjusting of said weighting factor is based on the correctness of said quantity for said previous measurements.

15. A method according to claim 1 wherein said quantity is a cost function wherein multi-element vectors are combined to give a single scalar number which is the said quantity.

16. A method according to claim 1 wherein said quantity is determined by adaptive analysis wherein reward and punish signals are introduced to affect said quantity.

17. A method according to claim 1 wherein the quantity $X_j$ is a cost function wherein the weighting function is selected by measuring statistical scatter parameters.

18. A method according to claim 1 wherein the weighting function is derived by an adaptive analysis in which weighs initially are set to random values and a learning procedure is performed wherein reward and punish signals are introduced to modify the weighting function.

19. A system to measure at least one of the geometric and the electromagnetic characteristics of an object, that comprises:
means for directing continuous wave energy of a single frequency upon the object which interacts with same, without mechanically vibrating the object, to provide continuous wave energy that emanates from the object;
means for detecting the wave energy which emanates from said object by virtue of the wave energy directed thereupon by an array of spacsd apart wave energy sensors to provide signals;
means for processing the signals from each wave energy sensor into at least one of amplitude and phase information for each said sensor;
means for combining said at least one of amplitude and phase information of the array of sensors to provide a single scalar quantity which represents at least one of said geometric and electromagnetic characteristics of said object, said means for combining providing the single scalar quantity by a cost function wherein multi-element vectors are combined to give said single scalar quantity; and
means for accepting or rejecting said object based on said quantity.

20. A system as claimed in claim 19 wherein said means for accepting or rejecting is used to manipulate said object.

21. A system as claimed in claim 19 wherein said means for accepting or rejecting is used to guide the manipulation of said object along a predetermined trajectory.

22. A system as in claim 19 wherein said quantity is compared with previously determined quantities obtained in like manner from similar objects and said accepting or rejecting is based upon said comparison.

23. A system as in claim 22 wherein the accepting or rejecting decision is used to manipulate said objects.

24. A system as in claim 23 wherein the accepting or rejecting decision is used to guide the manipulation of said object along a predetermined trajectory.

25. A system according to claim 19 wherein the wave energy sensors are operable to detect electromagnetic wave energy from which an electromagnetic characteristic of the object can be derived.

26. A system according to claim 25 in which the sensors comprise inductive sensors.

27. A system according to claim 27 in which the sensors comprise capacitive sensors.

28. A system to measure at least one of a geometric characteristic and an electromagnetic characteristic of an object, that comprises:
means for directing continuous wave energy at a narrow band of frequencies upon the object which interacts with the wave energy;
means for detecting continuous wave energy emanating from the object at many discrete, spatially separated locations to provide electric signals;
means for processing the electric signals to derive amplitude and phase information therefrom for each spatially separated location; and
means for combining said amplitude and phase information for each spatially separated location to provide a single composite signal whose magnitude represents said at least one of the geometric characteristic and the electromagnetic characteristic of the object, said means for combining providing the single composite signal by a cost function wherein multi-element vectors are combined to give a single scalar number which is said composite signal.

29. A system according to claim 28 wherein said means for detecting is part of a gripper unit of a robot and serves to provide information to permit guidance of the gripper with respect to the object along a correct trajectory despite errors in either gripper or object position or orientation.

30. A system according to claim 29 wherein the means for detecting also provides information to permit proper manipulation of the object.

31. A method of measuring at least one characteristic quantity representative of geometric form and electromagnetic properties of an object, that comprises:
generation a continuous electromagnetic field in the vicinity of an object whose characteristic is to be measured, said electromagnetic field having a narrow frequency range;

detection at a plurality of spaced apart locations within said electromagnetic field electrical signals in said narrow frequency range resulting from interaction of said field with said object;

processing said electrical signals detected at each of said locations to derive amplitude and phase information for each of said locations;

combining said amplitude and phase information from said plurality of locations to provide a characteristic quantity which represents said geometric form and electromagnetic properties of said object; and acting upon said object on the basis of said quantity;

wherein an acoustic field having a narrow frequency band is generated as a continuous wave and applied to said object, the resultant acoustic waves in the same frequency band which interact with said object are detected at a plurality of spaced apart locations, and amplitude and phase information from each of said plurality of locations is combined to generate a quantity representative of a geometric property and said object is acted upon in response to both said electromagnetic and acoustic field interactions therewith.

32. The method of claim 31 wherein said acoustic and electromagnetic fields simultaneously interact with said object.

33. The method of claim 31 wherein said acoustic and electromagnetic fields are selectively applied to said object.

34. A system to measure at least one of a geometric characteristic and an electromagnetic characteristic of an object, that comprises:

means for directing continuous wave energy at a narrow band of frequencies upon the object which interacts with the wave energy;

means for detecting continuous wave energy emanating from the object at many discrete, spatially separated locations to provide electric signals;

means for processing the electric signals to derive amplitude and phase information therefrom for each spatially separated location; and means for combining said amplitude and phase information for each spatially separated location to provide a single composite signal whose magnitude represents said at least one of the geometric characteristic and the electromagnetic characteristic of the object, wherein said means for combining provides the composite signal by adaptive analysis wherein reward and punish signals are introduced to affect said composite signal.

35. A system to measure at least one of the geometric and the electromagnetic characteristics of an object, that comprises:

means for directing continuous wave energy of a single frequency upon the object which interacts with same, without mechanically vibrating the object, to provide continuous wave energy that emanates from the object;

means for detecting the wave energy which emanates from said object by virtue of the wave energy directed thereupon by an array of spaced apart wave energy sensors to provide signals;

means for processing the signals from each wave energy sensor into at least one of amplitude and phase information for each said sensor;

means for combining said at least one of amplitude and phase information of the array of sensors to provide a single scalar quantity which represents at least one of said geometric and electromagnetic characteristics of said object, said means for combining providing the single scalar quantity as a composite signal by adaptive analysis wherein reward and punish signals are introduced to affect said composite signal; and means for accepting or rejecting said object based on said quantity.

* * * * *